(12) United States Patent
Henein et al.

(10) Patent No.: US 11,497,445 B2
(45) Date of Patent: Nov. 15, 2022

(54) SENSOR SYSTEM

(71) Applicant: Ecole Polytechnique Fédérale de Lausanne (EPFL), Lausanne (CH)

(72) Inventors: Simon Henein, Neuchatel (CH);
Charles Baur, Saint-Aubin (CH);
Thomas Fussinger, Zürich (CH);
Hubert Schneegans, Saint-Aubin (CH);
Lisa Bonnefoy, Saint-Aubin (CH)

(73) Assignee: ECOLE POLYTECHNIQUE FÉDÉRALE DE LAUSANNE (EPFL), Lausanne (CH)

( * ) Notice: Subject to any disclaimer, the term of this patent is extended or adjusted under 35 U.S.C. 154(b) by 449 days.

(21) Appl. No.: 16/802,599

(22) Filed: Feb. 27, 2020

(65) Prior Publication Data

US 2020/0268320 A1   Aug. 27, 2020

(30) Foreign Application Priority Data

Feb. 27, 2019   (EP) ..................................... 19159811

(51) Int. Cl.
*A61B 5/00* (2006.01)
*A61B 5/11* (2006.01)
*G01L 5/00* (2006.01)

(52) U.S. Cl.
CPC .............. *A61B 5/6817* (2013.01); *A61B 5/11* (2013.01); *G01L 5/0028* (2013.01)

(58) Field of Classification Search
CPC ........ A61B 5/6817; A61B 5/11; G01L 5/0028
See application file for complete search history.

(56) References Cited

U.S. PATENT DOCUMENTS

2010/0328675 A1* 12/2010 Bertholds .............. A61B 90/06
356/498

FOREIGN PATENT DOCUMENTS

| EP | 2 255 170 | 12/2010 |
|---|---|---|
| EP | 2 626 680 A1 | 8/2013 |
| EP | 2 626 6801 B1 | 10/2015 |
| WO | WO2015/168698 | 11/2015 |

OTHER PUBLICATIONS

European Search Report—EP 19 15 9811—dated Oct. 24, 2019.

* cited by examiner

*Primary Examiner* — Patrick Fernandes
*Assistant Examiner* — Severo Antonio P Lopez
(74) *Attorney, Agent, or Firm* — Nixon & Vanderhye

(57) ABSTRACT

Sensor system comprising a frame supporting a force-sensing tip arranged to generate a signal based upon a force applied by said force-sensing tip to a material to be tested, the system further comprising:
an input drum mounted in said frame such that it can rotate about an input axis of rotation;
an output lever supported by said frame by means of an output revolute joint defining an output axis of rotation;
wherein said force-sensing tip is mounted on said output lever such that said force-sensing tip is arranged to be brought into contact with a material to be tested;
and wherein said sensor system comprises a mechanical transmission arranged to kinematically link said input drum to said output lever such that a rotation of said input drum about said input axis of rotation causes said output lever to pivot in an oscillatory manner about said output axis of rotation.

17 Claims, 3 Drawing Sheets

SENSOR SYSTEM

TECHNICAL FIELD

The present invention relates to the technical field of sensor systems. More particularly, it relates to a force sensor for measuring small forces applied to materials, particularly but not exclusively to biological tissues.

STATE OF THE ART

The human ear consists of three parts: the outer ear (ear canal and eardrum), the middle ear (auditory tube and the three ossicles) and the inner ear (see FIG. 1). The sound wave passes through the ear canal and vibrates the tympanic membrane. The movement of the eardrum is then transmitted by the ossicles to the inner ear before being transformed into electrical signals.

Some diseases are responsible for the partial or total destruction of ossicles (e.g. ear infections and cholesteatoma) or loss of mobility (e.g. otosclerosis). These pathologies of the middle ear lead to a hearing loss.

A decrease in sound perception may also be due to a dysfunction of the inner ear. Doctors use hearing tests or complementary examinations (MRI, verification of the ossicular chain mobility) to establish a complete diagnosis.

In case of middle ear surgery, the surgeon may have to replace one or more elements of the middle ear with prostheses. During the operation, the skin at the base of the tympanic membrane is incised and lifted to provide access to the middle ear. The surgeon applies forces to evaluate the stiffness and mobility of the ossicular chain). This information can be used per-operatively to qualify and quantify the disease and therefore determine the best cure, as well as to validate surgical processes and related outcomes. Once the prosthesis is installed, the surgeon follows the same approach to check the ossicular chain mobility to ensure that the placement was correctly performed.

The PalpEar, developed by Sensoptic, is described in the patent EP2626680, and is illustrated in the lower part of claim 3. This device is a tool for middle ear surgery with an optical force sensor integrated therein, used as illustrated in FIG. 2. A standard 45° Storz tip (see the upper device on FIG. 3) is combined with a triaxial optical sensor used to measure the force applied by the surgeon at the end of the tool. The surgeon can thus rely on this feedback to estimate the level of mobility of the ossicles.

However, the disadvantage of this system is the lack of information on the displacement generated during palpation. The notion of mobility remains a subjective assessment from the surgeon especially as the displacement to be generated (of the order of several microns) and the force to be measured range (mN) are close to the limit of, or are even beyond, human (surgeon) capabilities.

An aim of the present invention is hence to at least partially overcome the above-mentioned drawbacks of the prior art.

DISCLOSURE OF THE INVENTION

More specifically, the invention relates to a sensor system as defined in claim 1. This sensor system comprises a frame (e.g. a hollow tubular frame) supporting a force-sensing tip arranged to generate a signal based upon a force applied by said force-sensing tip according to one, two or three axes.

According to the invention, the system further comprises:
an input drum mounted inside said frame such that it can rotate about an input axis of rotation;
an output lever supported by said frame by means of an output revolute joint (which may be for instance a pinned hinge joint or a flexure pivot such as a remote centre compliance RCC pivot) having one degree of freedom in rotation and hence defining an output axis of rotation which is ideally perpendicular to said input axis of rotation.

Said force-sensing tip is mounted on said output lever such that said force-sensing tip, particularly a distal extremity thereof, is arranged to be brought into contact with a material to be tested, for instance a biological material such as an ossicle.

Furthermore, said sensor system comprises a mechanical transmission arranged to kinematically link said input drum to said output lever such that a rotation of said input drum about said input axis of rotation causes said output lever to pivot in an oscillatory manner (i.e. back and forth) about said output axis of rotation.

As a result, by pivoting said input drum, a predetermined displacement of the distal extremity of the tip is generated, with a precise, known relationship between the input rotation and the output displacement. As a result, the user can calculate the resistance of the material on the basis of the known displacement of the distal extremity of the tip and the force measured by the tip rather than having to rely on feel and perception alone. This system is applicable more widely than simply for measuring the movement and resistance of ossicles, e.g. for hardness measurement of soft materials such as elastomers, rubbers, gels and so on.

Specific realisations and other advantageous details are described in the dependent claims, which can be combined in any manner which makes technical sense.

BRIEF DESCRIPTION OF THE DRAWINGS

Further details of the invention will appear more clearly upon reading the description below, in connection with the following figures which illustrate.

EMBODIMENTS OF THE INVENTION

Figure 1:
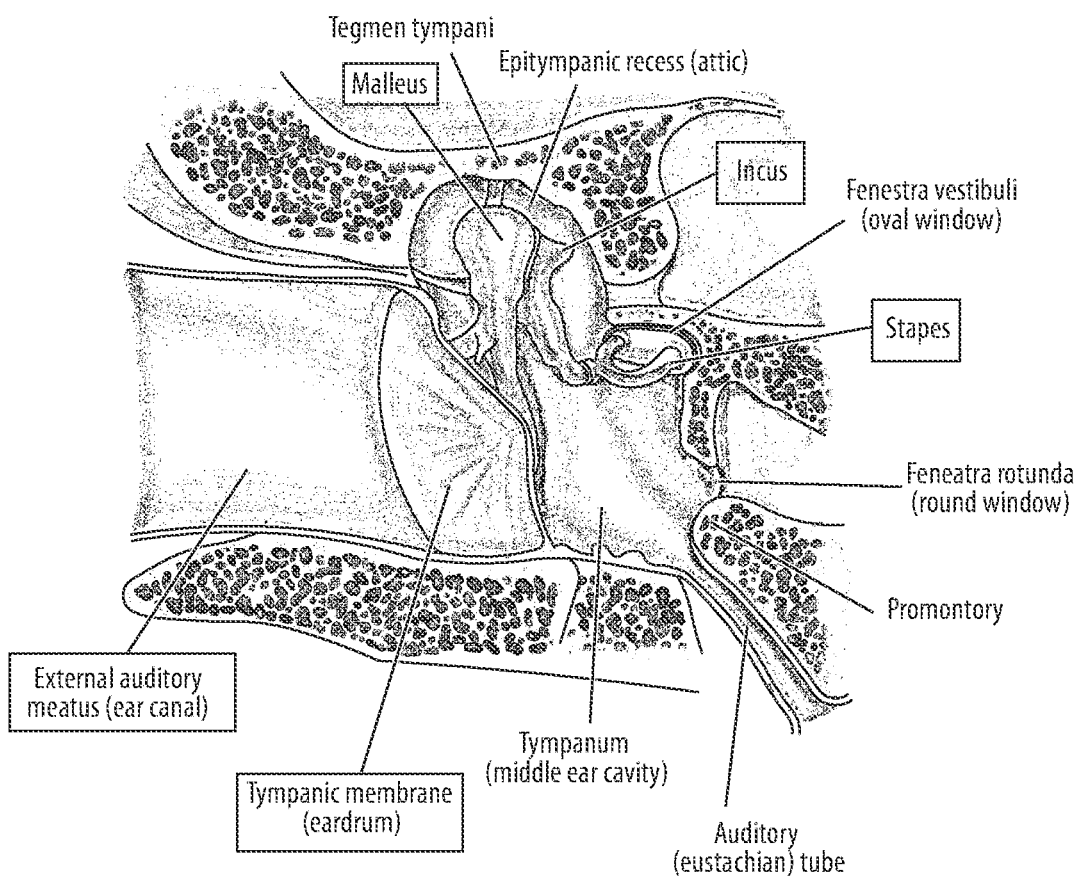
FIG. 1 is an illustration of the anatomy of a mammalian, in this case human, ear.
Figure 2:
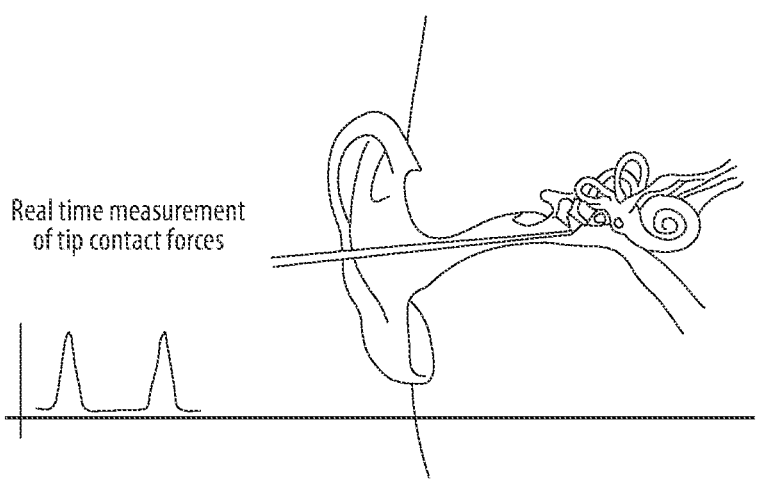
FIG. 2 is an illustration of the use of the PalpEar device.
Figure 3:
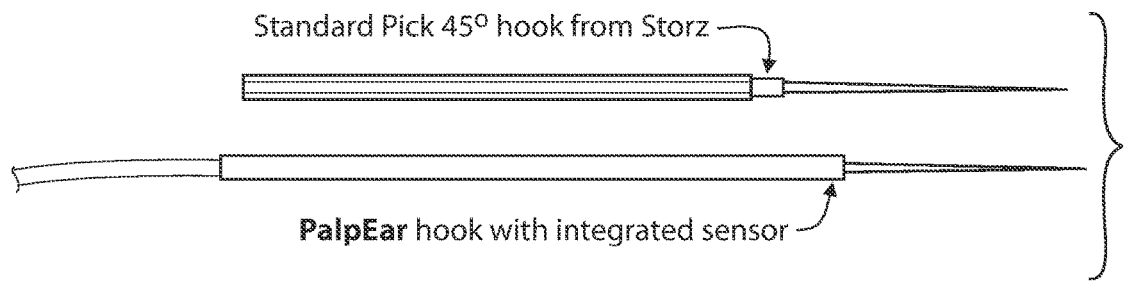
FIG. 3 is an illustration of a conventional Storz-type hook and a PalpEar device for testing the properties of body tissues, particularly ear tissues, more particularly ossicles.
Figure 4:
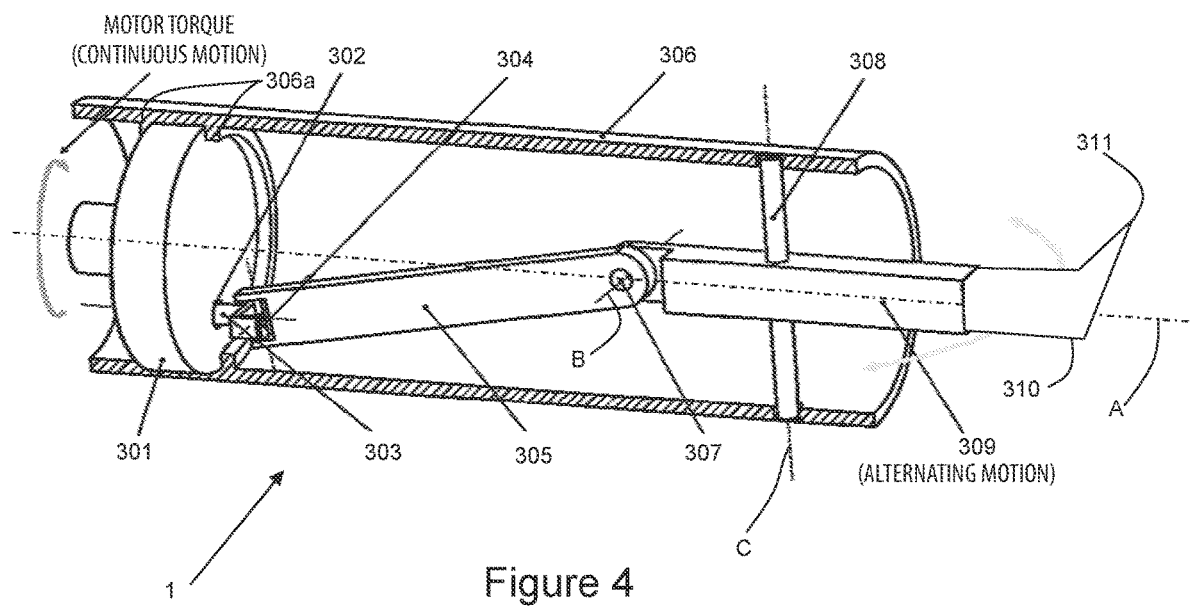
FIG. 4 is a partial schematic diagram of a first embodiment of a sensor system according to the invention.

FIG. 4 illustrates schematically a first embodiment of a sensor system 1 according to the invention, which clearly illustrates the kinematics upon which the device of the invention is based. The sensor system 1 is arranged to measure the force applied to a material in response to a displacement, this material being in particular a biological tissue, more particularly ossicles. However, the system 1 is applicable more widely, e.g. for hardness testing of soft materials such as rubbers, elastomers, gels and so on.

The device comprises a frame 306, illustrated here in the form of a cylindrical hollow tube. This frame 306 supports an input drum 301 by any convenient means (e.g. interior flanges 306a in the illustrated case), which is arranged to be driven about a first (input) axis of rotation A either mechanically, hydraulically, pneumatically or manually. This first axis A is coincident with the longitudinal axis of the frame 306, but this does not strictly have to be the case, the first axis A being offset therefrom linearly and/or angularly. The input drum 301 interacts with an off-centre (i.e. eccentric) pin 302 which may be fixed thereto or, as illustrated, be provided linked thereto via a cylindric joint. The pin 302 hence follows a rotary trajectory relative to the frame 306, orbiting around the axis A in a plane perpendicular thereto. A universal joint 303, 304 of any convenient type is provided between the off-centre pin 302 and a substantially rigid connecting lever 305, this latter being itself linked to an output lever 309 by means of a revolute connecting joint 307 such as a simple pinned joint as illustrated. This joint 307 defines a second (intermediate) axis of rotation B which is perpendicular to the first axis of rotation A. It should be noted that, alternatively, the off-centre pin 302 can be fixed to (or even monobloc with) the drum 301 and fitted with play or via a cylindric or other resilient joint into a corresponding opening in an element of the universal joint 303, 304.

The elements numbered 302, 303, 304, 305 and 307 hence constitute a mechanical transmission between input drum 301 and output lever 309, kinematically linking these two elements.

The output lever 309 is arranged to have one degree of freedom in rotation by being pivoted on the frame 306 by means of an output revolute joint 308, here illustrated as a pin which extends diametrically across the frame 306 so as to define a third (output) axis of rotation C which is perpendicular to the first axis of rotation A and to the second axis B. However, as will be seen below in the context of FIGS. 5 and 6, other types of revolute (i.e. one degree of freedom) joints are possible.

As a result, a rotation of the input drum 301 causes the output lever 309 to pivot back and forth about the third axis of rotation C within predefined angular limits and in a plane perpendicular to axis C.

Output lever 309 is provided with a force-sensing tip 110 e.g. of the type described in EP2626680 and EP2255170 (hereby incorporated by reference in their entireties) or any other convenient type (mechanical, piezoelectric, optical or similar, arranged to output an electrical, optical or other signal based on a force applied by or to said tip 310 according to one, two, three or more axes), which is arranged to be brought into contact with a material to be measured, such as but not limited to biological tissue, particularly ear tissue, more particularly ossicles in order to measure the resistance force generated in response to displacement of the tip 310 when it is brought into contact with the material in question. For ossicle-related measurements, a 0-100N, ideally 0-0.5 N measuring range with a resolution of e.g. 5 mn, ideally 2 mN is appropriate.

For small angular displacements of the output lever 309 around third axis C for which the small-angle-approximation holds (i.e. approximately ±12° either side of the first axis A), the distal end 311 of the tip 310 is substantially linear.

Since there is a kinematic, and indeed desmodromic relationship between the input drum 301 and the distal end 311 of the tip 310, a known input rotation of the drum 301 (measured e.g. by a well-known rotary encoder or similar) will cause a known substantially linear displacement of the distal end 311 in a plane parallel to axis A and perpendicular to axis C. As a result, the displacement of the distal end 311 of the tip 310 can be precisely known based on the rotational input to the drum 301.

It should be noted that the output lever 309 and/or the tip 310 can be sealed to the frame 306 by a seal of any convenient type (not illustrated) if required.

Since the diameter of the frame 306 may be very narrow, e.g. of the order of 2 mm in the case in which the sensor 1 is arranged to be able to be inserted into a human ear, the universal and pinned joints illustrated in FIG. 4 may not be appropriate in certain situations since they may be difficult or impossible to construct for manufacturing reasons.

Figure 5:
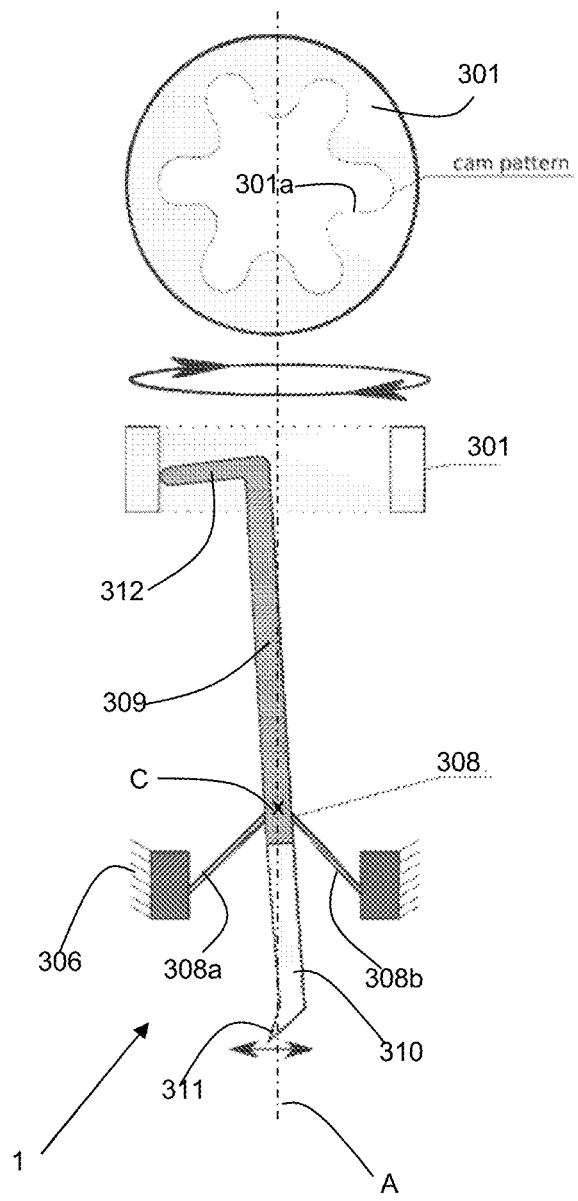
FIG. 5 is a partial schematic diagram of a second embodiment of a sensor system according to the invention.
Figure 6:
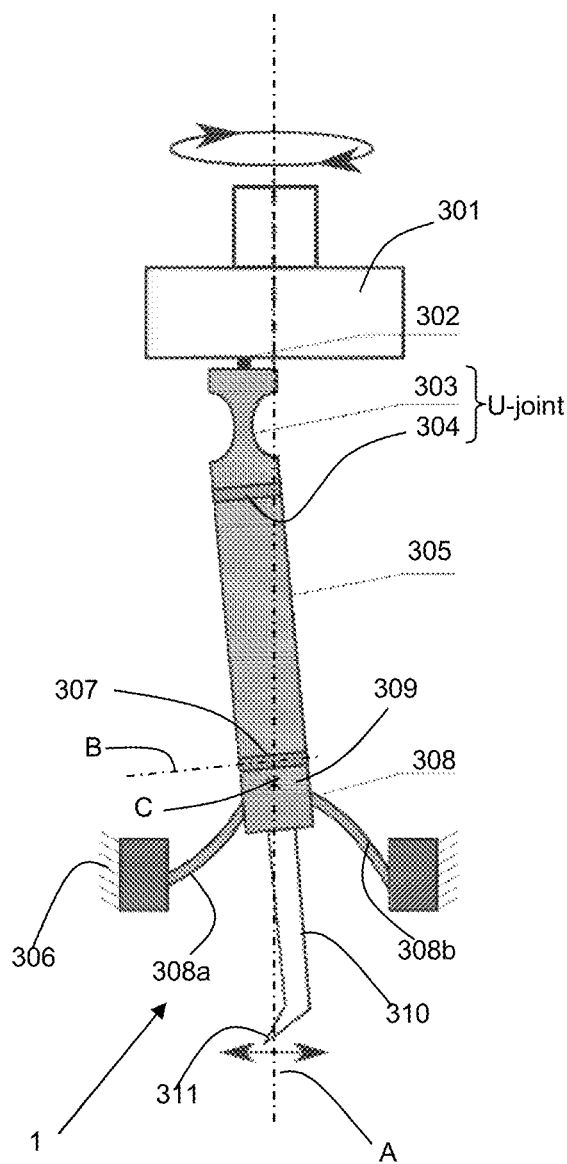
FIG. 6 is a partial schematic diagram of a third embodiment of a sensor system according to the invention.

FIGS. 5 and 6 illustrate schematically partial views of advantageous solutions to this issue, based around micromachining and/or additive manufacturing, e.g. using femto laser printing technology or other additive manufacturing techniques. Since little assembly is required, this significantly reduces the cost of the sensor 1, and also allows to reach a suitable system dimension (diameter <2 mm) for intra-aural use. The embodiments illustrated in these figures will be described below only insofar as they differ from that of FIG. 4.

In each of FIGS. 5 and 6, the connecting lever 305 is not present, and output lever 309 is pivoted on frame 306 by means of a flexure pivot system 308. Such pivots are described e.g. in "*The Art of Flexure Mechanism Design*", Florent Cosandier, Simon Henein, Murielle Richard and Lennart Rubbert, EPFL Press, 2017 (hereby incorporated by reference in its entirety), and typically comprise mechanisms constructed of flexures of the blade spring type, cols, torsion rods and so on. This flexure pivot 308 may be monobloc with the output lever 309, or this latter may be fixed thereto e.g. by force fitting, bonding, welding or similar.

In FIG. 5, the flexure pivot 308 defines revolute joint a one degree of freedom around axis of rotation C, which is formed as a Remote Centre Compliance (RCC) pivot which defines said axis C. To this end, the pivot 308 comprises a pair of blade springs 308a, 309a which, when unstressed, extend in respective planes parallel to the axis of rotation C and which intersect this latter.

In this embodiment, the input drum 301 (illustrated also in plan view at the top of the figure) comprises an internal cam surface 301a, and the output lever 309 further comprises a cam follower 312 which is maintained in contact with the cam surface 301a by means of a pre-stress of the flexure pivot 308. The mechanical transmission constituted by cam surface 301a and cam follower 312 is hence kinematic but not desmodromic in this case.

Cam follower 312 can be monobloc with the output lever 309 or a separate part fixed thereupon. In essence, this latter is constructed such that, in the absence of the input drum 301, the output lever 309 would be inclined at a greater angle to the first axis A than is illustrated. The flexure pivot 308 is hence arranged to bias the output lever 309 such that the cam follower is biased against the can surface 301a. Cam surface 301 can be of any convenient form, such as oval, polygonal, or with any convenient number of lobes (six are illustrated in FIG. 5, but the number can be two, three, four, five, six, seven, eight or even more). Alternatively, the input drum can have an exterior cam surface, the shape of the output lever 309 and the cam follower 312 being adapted in consequence. In either case, the input drum 301 can be offset such that the input axis A does not intersect the output axis C.

As a result, rotation of the input drum 301 causes the distal end 311 of the tip 310 to displace back and forth in its plane as described in the case of FIG. 4, this displacement being known based on the angular displacement of the input drum as before.

In the embodiment of FIG. 6, the input drum 301 comprises an eccentric pin 302 arranged facing the tip 310, as in FIG. 4. The pivot arrangement defining the axis of rotation C is as in FIG. 5, and need not be described further. In this embodiment, the universal joint 303, 304 the connecting rod 305, the revolute joint 307 (which defines second axis of rotation B), the output lever 309 and the flexure pivot arrangement 308 (defining axis of rotation B) are of monobloc construction. The universal joint 303, 304 is formed as a pair of col (notch) or blade flexures arranged to act at 90° to one another, a first flexure 303 arranged to permit bending parallel to axis C, the second flexure 304 arranged to permit bending perpendicular thereto. It does not matter which of flexures 303 and 304 is closest to the input drum 301.

Indeed, the flexure nearest the pin 302 can be a rotationally-symmetrical hour-glass shaped col with two degrees of freedom in bending.

The pin 302 is either fixed to the drum 301 and situated with play in a hole in the universal joint 303, or vice-versa.

Revolute joint 307 is again formed as a col or blade flexure so as to provide a degree of freedom in rotation in a plane perpendicular to axes A and C.

The embodiment of FIG. 6 hence acts in the same manner as that of FIG. 4, the pinned pivots having been replaced by equivalent flexure pivots.

The stroke and frequency of the distal end 311 of the tip 310 can be adjusted according to the surgeon's needs in order to apply an appropriate displacement, for instance by positioning the body 306 and the distal end 311 of the tip 310 as required and rotating the input drum 301 by an appropriate angle at an appropriate speed. The maximum stroke of the end 311 can be predetermined at manufacture by acting upon the lengths of the levers 305, 309, the position of the various pivots 303, 304, 307, 408 and the radial position of the pin 302 on the input drum 301 or the shape of the cam surface 301a as appropriate.

A safety system can be also arranged to ensure that no damage is caused to the material under test by preventing application of excessive force by the tip 310. Such a security system can for instance be achieved by integrating a bi-stable mechanism at the tip 110 which will cause the tip 110 to "spring" backwards in the case of excessive force being applied. Alternatively, a friction clutch, slip joint or similar can be placed so as to cause the tip 110 to "give" and displace with regard to the output lever 309 once a certain force has been exceeded.

Although the invention has been described in respect of specific embodiments, variations thereto are possible without departing from the scope of the appended claims. For instance, where certain axes of rotation have been described as being perpendicular to one another, this does not necessarily have to be so in situations in which such non-perpendicular axes will function adequately.

The invention claimed is:

1. A sensor system comprising a frame supporting a force-sensing tip arranged to generate a signal based upon a force applied by said force-sensing tip to a material to be tested, said sensor system further comprising:
an input drum mounted in said frame such that said input drum can rotate about an input axis of rotation;
an output lever supported by said frame by means of an output revolute joint defining an output axis of rotation;
wherein said force-sensing tip is mounted on said output lever such that said force-sensing tip is arranged to be brought into contact with the material to be tested;
and wherein said sensor system comprises a mechanical transmission arranged to kinematically link said input drum to said output lever such that a rotation of said input drum about said input axis of rotation causes said output lever to pivot in an oscillatory manner about said output axis of rotation.

2. The sensor system according to claim 1,
wherein said mechanical transmission comprises a connecting lever arranged to interact with the input drum at a point on said input drum which is eccentric with respect to the input axis via a universal joint having two degrees of freedom in bending,
and which is pivotally connected to said output lever via a revolute connecting joint defining an intermediate axis of rotation which is situated in a plane parallel to the input axis and perpendicular to the output axis.

3. The sensor system according to claim 2,
wherein said connecting lever, said universal joint and said output lever are monobloc.

4. The sensor system according to claim 2,
wherein both of said universal joint and said revolute connecting joint comprise at least one flexure pivot.

5. The sensor system according to claim 4,
wherein both of said universal joint and said revolute connecting joint comprise at least one flexure pivot.

6. The sensor system according to claim 1,
wherein said input drum comprises a cam surface,
and wherein the mechanical transmission comprises a cam follower integrated with said output lever, said cam follower being maintained in contact with said cam surface.

7. The sensor system according to claim 6,
wherein said cam follower and said output lever are monobloc.

8. The sensor system according to claim 1,
wherein said output revolute joint is defined by a flexure pivot system,
wherein said flexure pivot system is a remote centre compliance pivot.

9. The sensor system according to claim 8,
wherein said flexure pivot system and said output lever are monobloc.

10. The sensor system according to claim 1,
wherein said frame is adapted to be hand-held.

11. The sensor system according to claim 10,
wherein said frame is substantially tubular.

12. The sensor system according to claim 11,
wherein said frame has a diameter of 3 mm or less.

13. The sensor system according to claim 12,
wherein the diameter of said frame is 2 mm or less.

14. The sensor system according to claim 1,
further comprising a force limiter adapted to prohibit application of an excessive force to said material by said tip.

15. The sensor system according to claim 1,
wherein said sensor system is adapted for taking measurements of biological tissue.

16. The sensor system according to claim 15,
wherein said sensor system is adapted for intra-aural use.

17. The sensor system according to claim 16,
wherein said material is an ossicle.

* * * * *